Figure 1:
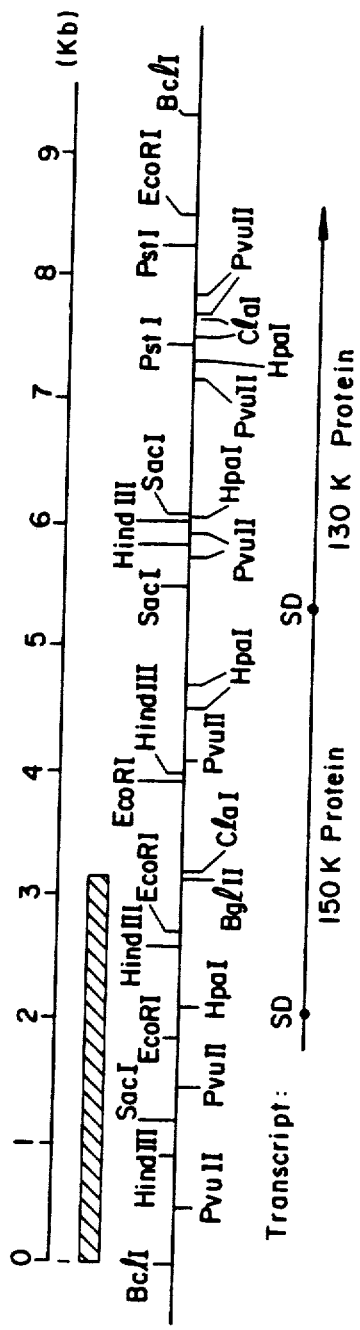

United States Patent [19]

Udaka et al.

[11] Patent Number: 4,994,380
[45] Date of Patent: Feb. 19, 1991

[54] PROCESS FOR EXPRESSING GENES BY BACILLUS BREVIS

[75] Inventors: Shigezo Udaka; Norihiro Tsukagoshi; Hideo Yamagata, all of Nagoya, Japan

[73] Assignee: Shigezo Udaka, Nagoya, Japan

[21] Appl. No.: 928,125

[22] Filed: Nov. 7, 1986

[30] Foreign Application Priority Data

Nov. 7, 1985 [JP] Japan ............................ 60-248036
Mar. 6, 1986 [JP] Japan ............................ 61-47273

[51] Int. Cl.$^5$ .................... C12N 15/00; C12N 1/20; C12P 21/00
[52] U.S. Cl. ............................ 435/69.1; 435/172.3; 435/833; 435/252.5; 435/202; 536/27; 935/77; 935/38
[58] Field of Search ............... 435/833, 172.3, 69.1, 435/252.5; 935/27, 38; 536/27

[56] References Cited

U.S. PATENT DOCUMENTS 4,695,546 9/1987 Aiba .............................. 435/172.3

FOREIGN PATENT DOCUMENTS 60-58073 4/1985 Japan .
60-58074 4/1985 Japan .
60-188073 9/1985 Japan .

OTHER PUBLICATIONS

Tsuboi, A. et al., Oct. 1986, J. Bacteriology 168(1), 365-373.
Marahiel, M. A. et al., 1980, "Characterization of a Plasmid from *Bacillus brevis* ATCC 9999", Adv. Biotech. 3:43-9.
Marahiel, M. A. et al., 1981 "Characterization of Chromosomal & Membrane Associated Plasmid in *Bacillus brevis* ATCC 9999", J. Antibact. 34(3), 323-30.
Dobritsa, A. P. et al., 1978, "Isolation and Characterization of Plasmid from *Bacillus brevis* Var. G.-B. Cells," Mol. Gen. Genet. 164(2) 196.

Watson, J. D. et al., 1983, *Recombinant DNA A Short Course*, pp. 86-90.
Kop, J., et al., 1984, J. Biol. Chem., 259, 15287-15293.
Yamagata, H. et al., (1985), "A Stable Plasmid Vector and Control of Its Copy Number in *Bacillus brevis* 47", Appl. Envirn. Microbiol., 49:1076.
Yamagata, H. et al., (1984), "Detection of Plasmids in *Bacillus brevis* & Introduction of a Plasmid into *B. brevis* 47", Agric. Biol. Chem. 48:1069.
Takahashi, W. et al., 1983, "Genetic Transformation of *Bacillus brevis* 47, A Protein Secreting Bacterium, by Plasmid DNA", J. Bact. 156(3)1130.

*Primary Examiner*—Richard A. Schwartz
*Assistant Examiner*—Michelle S. Marks
*Attorney, Agent, or Firm*—Armstrong, Nikaido, Marmelstein, Kubovcik & Murray

[57] ABSTRACT

An improved vector for expression in *Bacillus brevis* having:

(1) a nucleotide sequence (a) represented by a general formula MNOACP;
(2) a nucleotide sequence (b) located in the downstream of the nucleotide sequence (a) and represented by a general formula QRSWXY;
(3) a nucleotide sequence (c) located in the downstream of the nucleotide sequence (b) and acting as a binding site to ribosome in the cell of *Bacillus brevis*;
(4) a nucleotide sequence (d) located in the downstream of the nucleotide sequence (c) and acting as a translation initiation condon in the cell of *Bacillus brevis*; and
(5) a gene directly connected with the nucleotide sequence (d) and to express in the cell of *Bacillus brevis*;

wherein M represents G or T; N represents C, T or A; O represents A, C or T; P represents T or G; Q represents T or A; R represents T or A; S represents T, C or A; W represents A or G; X represents A or C; and Y represents T or G; and furthermore, wherein A represents adenine, C cytosine, G guanine and T thymine.

9 Claims, 5 Drawing Sheets

FIG. 3

```
                                                                        PvuII                                         60
CAGCTGGAGAGCTATCGCTTGAAAAATTTGCGTTATGAAAATGAAGTTGCGACGACTTTA

RsaI         AluI      120
GAGGTCATTCAATCGGAAGAAACATTGTCTACTCGTGAGAATGCGTACCAAAAAGCTATC

180
CTGTCTTACAACTTGGCTGTTGTAAACTTTGAAAATGCATTAGGAAATTAACCTAATTCA

-35                             240
AGCAAGATTATGAGGTTTTGAACCAAATTGGAAAAAGGTTCAGTCGTGACAGCCCGCCAT

-10    P1 ——▶                            RsaI                                 300
ATGTCCCCTATAATACGGATTGTGGCGGATGTCACTTCGTACATAATGGACAGGTGAATA

-35                          360
ACGAACCACGAAAAAAACTTTAAATTTTTTCGAAGGCGCCGCAACTTTTGATTCGCTCA

-10    P2 ——▶                                             -35   EcoRI    420
GGCGTTTAATAGGATGTCACACGAAAAACGGGGAATTGTGTAAAAAAGATTCACGAATTC

-10    P3 ——▶                                 -35           480
TAGCAGTTGTGTTACACTAGTGATTGTTGCATTTTACACAATACTGAATATACTAGAGAT

490    -10    500  P4 ——▶  510        520       530            540
TTTTAACACAAAAGCGAGGCTTTCCTGCGAAAGGAGGTGACACGCGCTTGCAGGATTCG
                                Ribosome binding site    fMet GlnAspSer 550        560         570          580         590            600
GGCTTTAAAAAGAAAGATAGATTAACAACAAATATTCCCCAAGAACAATTTGTTTATACT
GlyPheLysLysLysAspArgLeuThrThrAsnIleProGlnGluGlnPheValTyrThr 610       620         630   HpaI  640         650            660
AGAGGAGGAGAACACAAGGTTATGAAAAAGGTCGTTAACAGTGTATTGGCTAGTGCACTC
ArgGlyGlyGluHisLysValMetLysLysVal ValAsnSerValLeuAlaSerAlaLeu
Ribosome binding site
         670        680         690          700         710   AluI    720
GCACTTACTGTTGCTCCAATGGCTTTCGCAGCAGAAGAAGCAGCAACTACTACAGCTCCA
AlaLeuThrValAlaProMetAlaPheAlaAlaGluGluAlaAlaThrThrThrAlaPro 730       740         750          760         770          780
AAAATGGACGCTGATATGGAAAAAACCGTAAAACGTCTGGAAGCTCTTGGCCTGGTAGCA
LysMetAspAlaAspMetGluLysThrValLysArgLeuGluAlaLeuGlyLeuValAla
```

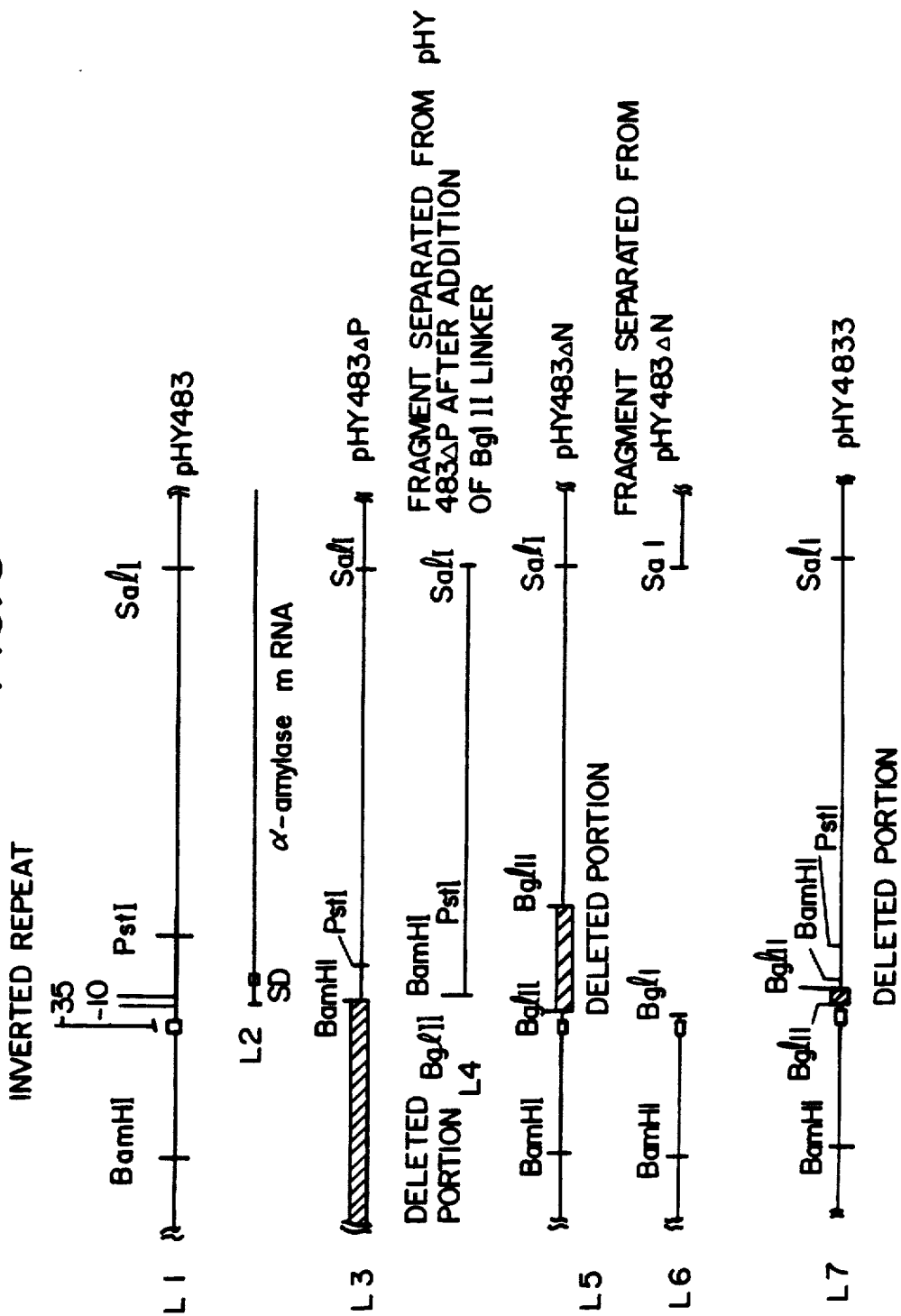

PROCESS FOR EXPRESSING GENES BY BACILLUS BREVIS

This invention relates to a method for expressing genes by *Bacillus brevis*.

When a certain gene is to be expressed by recombinant DNA technique using prokaryote, it seems that choice of a host and also choice of a vector suited for the host are very important. *Bacillus brevis* secretes a large amount of protein to the exterior of the cell thereof and thus secreted protein is of an very low protease activity, therefore *Bacillus brevis* is suitable for employing as the host. However, the *Bacillus brevis* has not hitherto been used as the host, because a suitable plasmid vector has not been prepared by recombinant DNA technique.

The inventors fixed their attention to the fact that *Bacillus brevis* has an excellent property as mentioned above when used for the host, and have devoted deep studies to exploit vectors suited for introducing into *Bacillus brevis*. As the result, the inventors have found that a structural gene can be well expressed by *Bacillus brevis*, when *Bacillus brevis* is transformed with a plasmid which can replicate in *Bacillus brevis* and includes a nucleotide sequence (a) represented by a general formula MNOACP; a nucleotide sequence (b) located in the downstream of the nucleotide sequence (a) and represented by a general formula QRSWXY; a nucleotide sequence (c) located in the downstream of the nucleotide sequence (b) and acting as a binding site to ribsome in the cell of *Bacillus brevis*; a nucleotide sequence (d) located in the downstream of the nucleotide sequence (c) and acting as a translation initiation codon in the cell of *Bacillus brevis*; and a gene directly connected with the nucleotide sequence (d) and to express in the cell of *Bacillus brevis*.

In the said general formulas, M represents G or T; N represents C, T or A; O represents A, C or T; P represents T or G; Q represents T or A; R represents T or A; S represents T, C or A; W represents A or G; X represents A or C; and Y represents T or G; and furthermore, wherein A presents adenine, C cytosine, G guanine and T thymine. "Downward" used herein means the downward when a structural formula of DNA is written consecutively along a line with the 5'-side of deoxyribose therein standing on the upward side and 3'-side thereof on the downward side.

Each of the nucleotide sequences (a) and (b) has a function as a transcriptional promoter. Preferable examples of the nucleotide sequence (a) are (1) GCAACT, (2) TTCACG and (3) TATACT, and preferable examples of the nucleotide sequence (b) are (1) TTTAAT, (2) TACACT and (3) AAAGCG. It is preferable that there are 17 base pairs between the nucleotide sequences (a) and (b) in case of the said preferable examples, however, there may be 15-20 base pairs between both nucleotide sequences. The nucleotide sequence (c) acts as a binding portion to ribosome and means what is called the Shine-Dalgarno sequence. The nucleotide sequence (d) acts as a translation initiation codon, and means normally the nucleotide sequence of ATG or TTG.

In order to express a structural gene derived from different species under control of the above promoters, it is required that the ligation be carried out so as to locate the nucleotide sequences (c) and (d) between the promoter nucleotide sequence (b) and the structural gene. In order to locate the nucleotide sequences (c) and (d) between the promoter sequence (b) and the structural gene, it is preferable that the structural gene is inserted into a plasmid vector having originally therein both the ribosome binding portion and the translation initiation codon. Alternatively, it may be possible that a structural gene having therein both the ribosome binding portion and the translation initiation codon is inserted in a plasmid vector. In a case wherein use is made of a plasmid vector including neither the ribosome binding portion nor the translation initiation codon nor both of them, a structural gene having therein either the ribosome bonding portion or the translation initiation codon or both of them must be inserted in the plasmid vector, otherwise either the ribosome binding portion or the translation initiation codon must be additionally inserted in the plasmid vector. Use may be made of a vector having therein a DNA sequence corresponding to signal peptide.

The structural gene may have therein a further native promoter sequence. Moreover, use may be made of the structural gene having therein a DNA sequence corresponding to signal peptide.

It is not required that use be made of a specific strain selected from *Bacillus brevis*. Preferable examples of *Bacillus brevis* are *Bacillus brevis* 47 FERM-P7224 and 481 FERM-P7531 (International deposit numbers FERM BP-1123 and FERM BP-1124).

When the plasmid vector in which the structural gene has been inserted is introduced in a cell of *Bacillus brevis* according to the present invention, the resulting microorganism has been transformed to be able to produce a large amount of useful materials such as proteins and so on.

The conventional methods can be used for inserting the structural gene into the plasmid vector and also for transducing thus obtained plasmid into *Bacillus brevis* using a recombinant DNA according to the present invention. For the structural gene, use can be made of not only a gene derived from eukaryote but also that from prokaryote. For example, use can be made of human gene (i.e. interferon, insulin, etc.), an enzyme protein gene of microorganism (tryptophanase, aspartate ammonia-lyase etc.) and so on.

By way of an example the present invention is further particularly explained hereinbelow.

EXAMPLE 1

(1) Cloning of promoter region of the cell wall protein gene of *Bacillus brevis* 47:

FIG. 1 shows a restriction map of the cell wall protein gene and its vicinity, which is prepared by analyzing chromosomal DNA of *Bacillus brevis* 47 (FERM-P7224) according to Southern blot method (J. Mol. Biol. 98, 503-517 (1975)) using as a probe a DNA fragment coding for a part of the said cell wall protein (protein having a molecular weight of about 150,000, which is hereinafter referred to as 150K protein). The said DNA fragment was cloned by Tsukagoshi et al as lacking a promoter region of the gene coding 150K protein (J. Bacteriol., 158, 1054-1060 (1984)). Furthermore, the transcriptional direction and transcription initiating sites of this gene were determined as shown in FIG. 1, using a RNA extracted from *Bacillus brevis* 47 according to S1 Map Method (J. Biol. Chem., 256, 11905-11910 (1981)). In FIG. 1, a hatched area

  

indicates a DNA fragment region of 3100 base pairs (hereinbelow 1000 base pairs are referred to as Kb), and the characters written on the upper and lower sides of the middle line indicate restriction enzymes and sites cleaved by the respective restriction enzymes.

Figure 2:
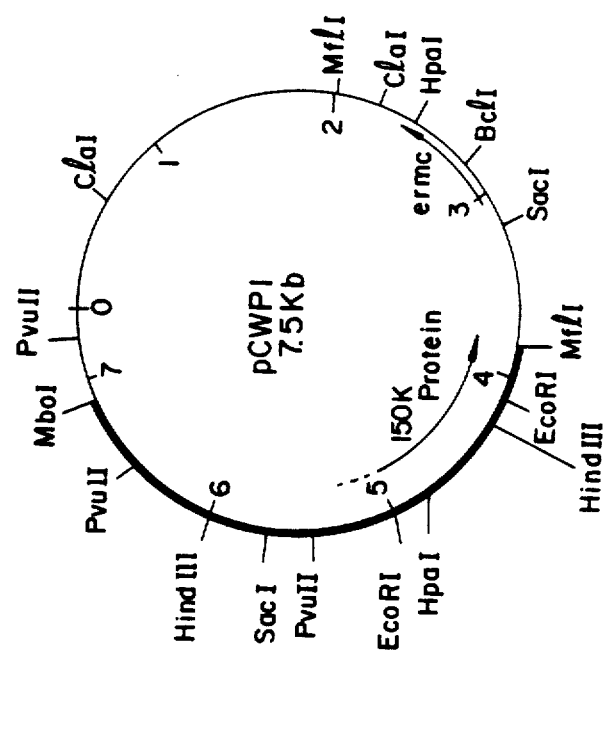

The chromosomal DNA from *Bacillus brevis* 47 was cleaved with the restriction enzyme BclI and then fractionated by agarose gel electrophoresis. 9 Kb BclI fragments (almost all length of DNA shown in FIG. 1) were eluted electrophoretically from the corresponding fractions. The eluted DNA fragments were then cleaved with the restriction enzyme BglII, and the resulting 3.1 Kb fragments were collected in the same manner as mentioned above, which were corresponding to the region hatched in FIG. 1. On the other hand, pHW I DNA (J. Bacteriol, 150, 804–814 (1982)) was cleaved with the restriction enzyme HindIII, treated by DNA polymerase to have blunt ends, then BamHI linkers@ were added, and the resulting product was connected with the said DNA fragment of 3.1 Kb by T4 ligase to form a recombinant DNA. The recombinant DNA was used for transforming *Bacillus subtilis* RM 141 ($r_M m_M$ arg 15 leu B8 his AI rec E4) (Mol. Gen. Genet., 168, 111–115 (1979)). The transformants thus obtained were grown in regeneration agar medium containing erythromycin (10 μg/ml), and antibody to 150K protein prepared beforehand was added to the transformants, as the result there were found colonies in which strains were reacted with the antibody when detected by an Enzyme Immunoassay Method (Gene, 16, 149 (1981)), using horseradish peroxidase-conjugated protein A(E-Y Laboratories Inc.). The plasmid pCWP I was extracted from the reacted colonies and it was confirmed that the said 3.1 Kb fragment had been inserted, which is indicated by a thick line in FIG. 2 showing a restriction map of the plasmid pCWP I. FIG. 2 includes various characters such as HindIII, which indicate restriction enzymes and sites cleaved by the restriction enzymes, likewise in FIG. 1.

@ BamHI linkers: 5' CGGATCCG 3', 3' GCCTAGGC 5'.

(2) Analysis of cloned DNA fragment and strength of promoter activity:

Base sequence of the cloned DNA fragment was determined by Maxam Gilbert Method (Methods Enzymol., 65, 449–560 (1980)) and using a RNA extracted from *Bacillus brevis* 47, a transcription initiation site was determined by SI Map Method (J. Biol-Chem., 256 11905-11910 (1981)). As the result, the inventors have found an open reading frame extending from the site at a distance of about 2 Kb from BclI site towards BglII site and four transcription initiation sites P1, P2, P3 and P4 located in the upstream of the open reading frame as shown in FIG. 3.

Incidentally, FIG. 3 shows a nucleotide sequence of the 5'-region of cell wall protein gene of *Bacillus brevis* 47, transcription initiation sites indicated by an arrow, and an amino acid sequence corresponding to the open reading frame which have now been found by the inventors. In FIG. 3, the mark indicates a promoter region and the mark indicates a translation initiation codon, both of which have now been found by the inventors.

Table 1 shows the nucleotide sequences found in the site extending from −10 to −35 region in the upstream of each of the said four transcription initiation sites.

As the result of analysis by SI Map Method, it was confirmed that the transcription was initiated with a higher frequency at each of P2, P3 and P4 sites than at P1 site having a sequence similar to the consensus sequence and compared with the promoter in *Bacillus licheniformis* α-amylase gene (Paml). Table 2 shows strength of promoter activity assayed by SI Map Method, and from the Table 2 it becomes clear that the promoters P2, P3 and P4 are of higher activity than the promoter P1 and Pam 1.

TABLE 1

| | −35 region | −10 region |
|---|---|---|
| P1 | GTGACAGCCCGCCATATGTCCCCTATAATA | |
| P2 | GCAACTTTTGATTCGCTCAGGCGTTTAATA | |
| P3 | TTCACGAATTCTAGCAGTTGTGTTACACTA | |
| P4 | TATACTAGAGATTTTTAACACAAAAAGCGA | |
| Paml | TTGTTA | TACAAT |

Paml: promoter sequence of *Bacillus licheniformis* α-amylase gene.

TABLE 2

| Strength of promoter activity by SI Map Method | |
|---|---|
| Kind of promoter | Promoter activity |
| P1 | ± |
| P2 | + + |
| P3 | + + + |
| P4 | + + |
| Paml | ± |

Figure 4:
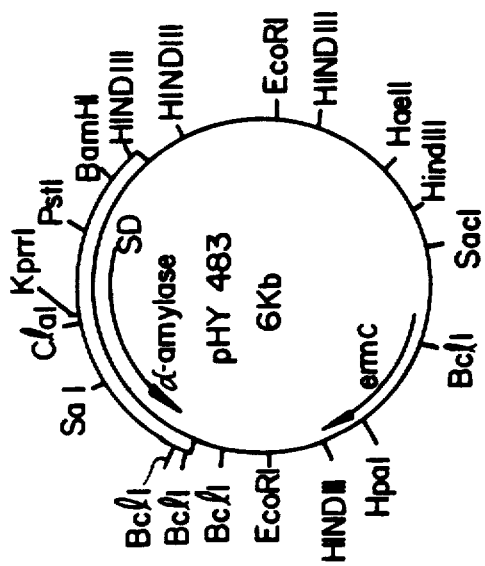

(3) Preparation of vector for use in assaying promoter activity in *Bacillus brevis* 47:

α-amylase gene was cloned from *Bacillus licheniformis* 584 strain (Arch. Biochem. Biophys., 155, 290–298 (1973)) and inserted into the plasmid vector pHY 481 which could be maintained stably in *Bacillus brevis* (Appl. Env. Microbiol., 49, 1076–1079 (1985)) to form the plasmid pHY 483 as shown in FIG. 4. It was confirmed that all nucleotide sequences in this amylase gene were generally the same as that of 5'-region of α-amylase gene in *Bacillus licheniformis* FDO2 strain (J. Bacteriol., 158, 369–372 (1984)), and the amylase gene was completely the same as the said α-amylase gene in respects of sequence in −10 region and −35 region, sequence in ribosome binding site (Shine-Dalgarno sequence), existence of inverted repeat sequence which is assumed to have the action to stop transcription from the gene located in the upstream, and so on. Using this gene a vector for use in assaying promoter activity was prepared in the manner as mentioned below.

At first, the plasmid pHY 483 was cleaved with rectriction enzyme BamHI, then a portion extending from the cleaved site to the site just prior to Shine-Dalgorno sequence in α-amylase gene was removed by nuclease Bal 31, whereto were added BamHI linkers, and the resulting products were made to a circular form to obtain the plasmid pHY 483ΔP. On one hand, the plasmid pHY 483 was cleaved with restriction enzyme PstI, then a portion extending from the cleaved site to the site at a distance of 270 base pairs from BamHI site in the downstream direction (i.e., to the site just prior to the inverted repeat sequence) was removed in the same manner, thereto were added BglII linkers@, subsequently the resulting product was circularized to obtain the plasmid pHY 483 ΔN. On the other hand, the plasmid pHY 483 ΔP DNA was cleaved with the restriction enzyme BamHI, treated by the DNA polymerase to have blunt ends, whereto were added the BglII linkers@, then cleaved witdh the restriction enzyme SalI, and thereafter separated by agarose gel electrophoresis to obtain a BglII-SalI fragment having 1.1 Kb and containing 5'-region of the amylase gene. Further, similarly pHY 483 ΔN DNA was cleaved with the restriction enzymes BglII and SalI to obtain a fragment of amylase gene, which lacked 5'-region thereof and had 4.7 Kb. Both fragments were ligated by T4 ligase to obtain the plasmid pHY 4833, which was just the same as that obtained from a transformed strain of *Bacillus brevis* 47. The plasmid pHY 4833 preserved the inverted repeat and Shine-Dalgarno sequences in the upstream of the amylase gene but lacked −35 and −10 regions as seen in FIG. 5. FIG. 5 is a diagram for explaining a process for preparing the plasmid vector pHY 4833 for use in detecting promoters, and shows regions of plasmids corresponding to the region extending over the sites to be cleaved with the restriction enzymes BamHI and SalI, which are shown in FIG. 4. In FIG. 5, □ indicates the inverted repeat sequence,

indicates the deleted portion, and the line L 2 indicates the site of Shine-Dalgarno sequence as well as the transcriptional direction of the α-amylase gene.
@ BglII linkers: 5'CAGATCTG3', 3'GTCTAGAC5'.

Figure 6:
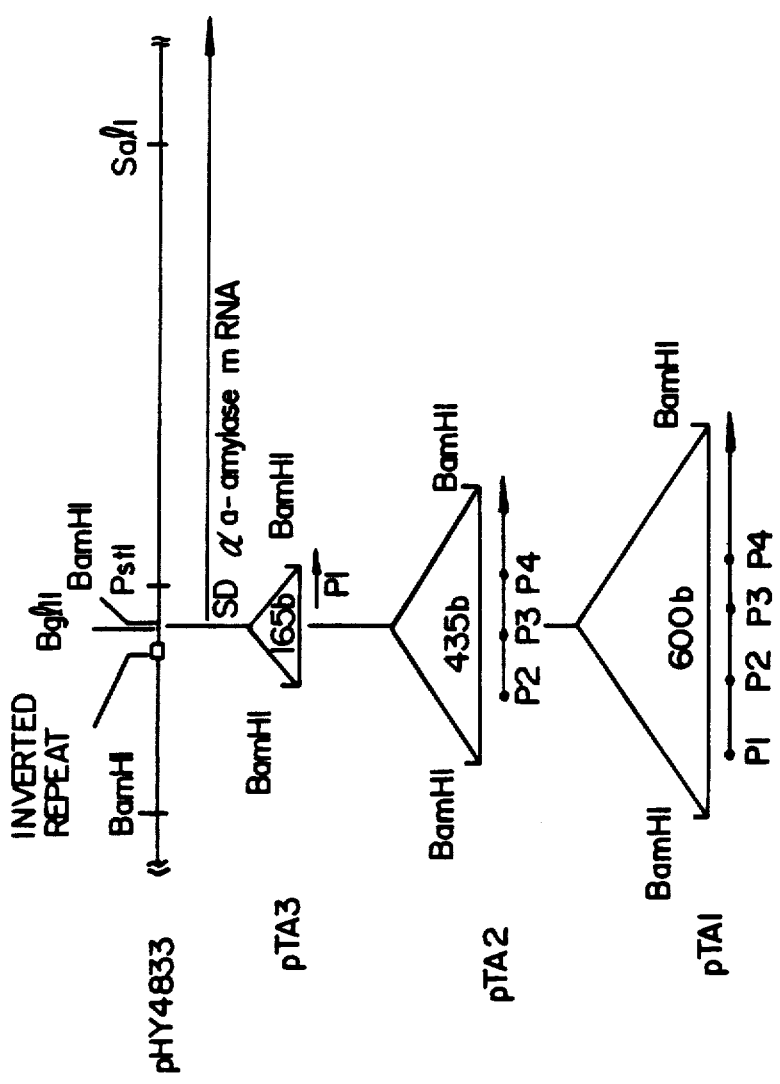

(4-1) Promoter activity of 5'-region of the cell wall protein gene using plasmid pHY 4833 in *Bacillus brevis* 47 as a host:

The 5'-region of cell wall protein gene was cleaved and separated to form an AluI-AluI fragment of 600 base pairs, an AluI-RsaI fragment of 165 base pairs and a RsaI-AluI fragment of 435 base pairs. More particularly, the AluI-AluI fragment was composed of the nucleotides from 116 to 715 including transcription initiation sites P1, P2, P3, P4 and their respective −10 and −35 regions, as shown in FIG. 3, the AluI-RsaI fragment was composed of the nucleotides from 116 to 280 including transcription initiation sites P1 and its −10 and −35 regions, and the RsaI-AluI fragment was composed of the nucleotides from 281 to 715 including transcription initiation sites P2, P3, P4 and their respective −10 and −35 regions. After BamHI linkers@were added to each of these fragments, each resultant fragment was inserted into BglII site of the plasmid pHY 4833 to obtain the plasmids pTA1, pTA3 and pTA2 as shown in FIG. 6. FIG. 6 shows 5'-region fragments of the cell wall protein gene, which were prepared by inserting each of the said respective fragments into the plasmid vector pHY 4833 for use in detecting promoter activity.
@ BamHI linkers 5'CGGATCCG3', 3'GCCTAGGC5'.

Each of the plasmids pHY 4833, pTA3, pTA3, pTA2, pTA1 was transduced into *Bacillus brevis* 47 to form the respective transformed strains, and each resulting transformant was incubated aerobically in T3 medium (soluble starch 2%, $MgCl_2.6H_2O$ 0.1%, yeast extract 0.4%, polypeptone 2%, meat extract 0.5%, uracil 0.01%, pH7) at 37° C. for 1 and 3 days, respectively, and then the amount of extracellular amylase was assayed by Saito's Method using soluble starch as a substrate (Arch. Biochem. Biophys., 155, 290-298 (1973)). Table 3 shows the respective extracellular amylase activity thus assayed.

TABLE 3

| Plasmid | Extracellular amylase activity ($\times 10^3$ units/ml) | |
|---|---|---|
| | 1 day cultivation | 3 day cultivation |
| pHY 4833 | 0.24 | 0.24 |
| pTA 3 | 0.17 | 0.16 |
| pTA 2 | 9.2 | 9.8 |
| pTA 1 | 7.8 | 10.0 |

Figure 7:
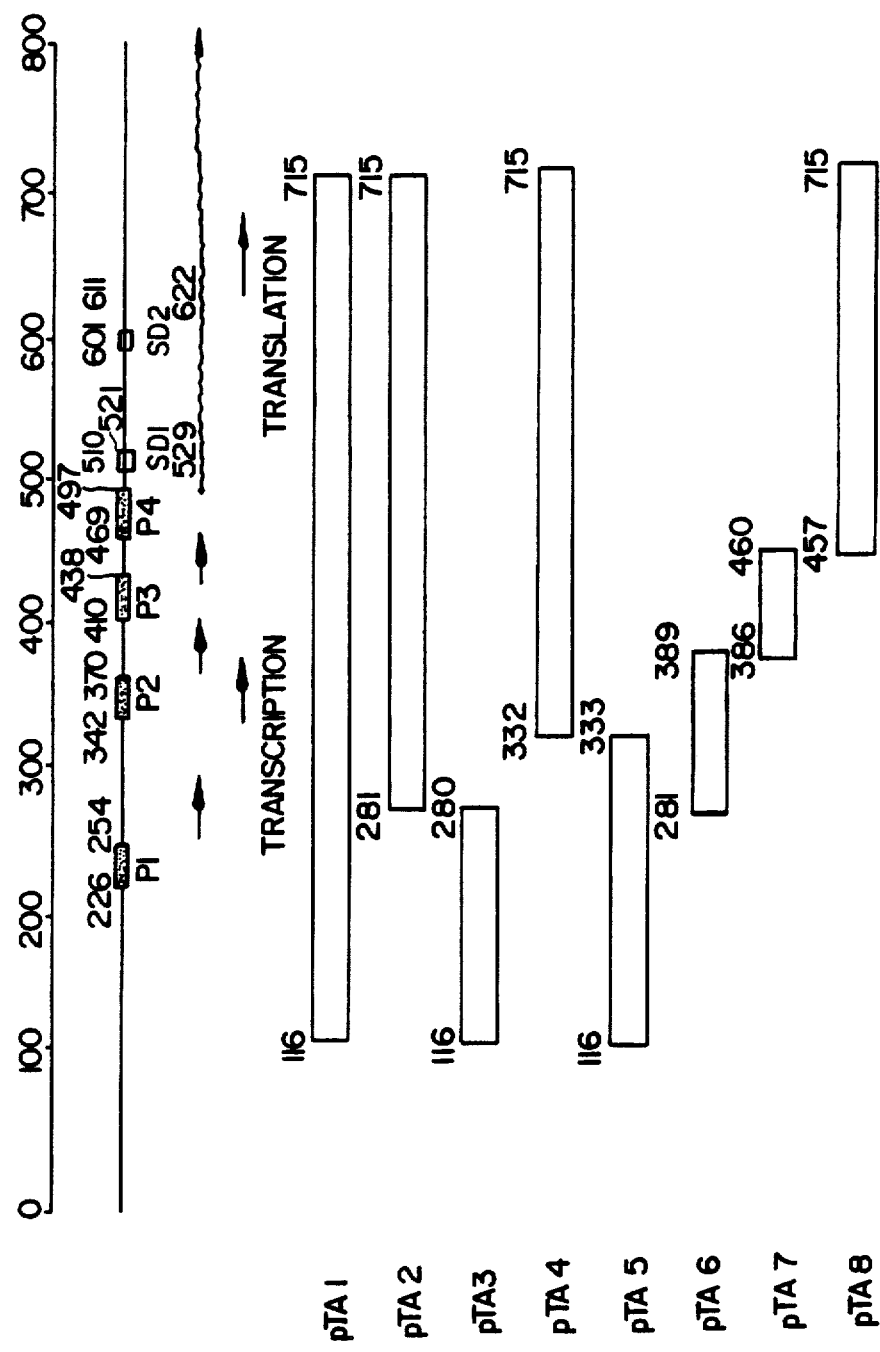

(4-2) Assay of promoter activity of 5'-region of cell wall protein gene using plasmid pHY 4833 in *Bacillus brevis* 47 as a host:

The cell wall protein gene was at first treated with various restriction enzymes or Bal 31 nuclease to shorten 5'-region of the gene, and then BamHI linkers@ were added to the shortened ends to prepare fragments. Each of the fragments was inserted into BglII site in the plasmid vector pHY 4833, which was for use in assaying promoter activity and was obtained in the preceding paragraph, and thus the plasmids pTA1-pTA8 were obtained as shown in FIG. 7. Each of the plasmids pTA1-pTA8 was introduced into *Bacillus brevis* 47, and each transformant was incubated aerobically in T3 medium (soluble starch 2%, $MgCl_2.6H_2O$ 0.1% $2.6H_2O$ 0.1%, yeast extract 0.4%, polypeptone 2%, meat extract 0.5%, uracil 0.01%, pH7) at 37° C., and the amount of extracellular amylase was assayed by Saito's Method using soluble starch as a substrate (Arch. Biochem. Biophys., 155, 290-298 (1973)) (Tagle 4).

Incidentally, the upper part of FIG. 7 shows sites of the promoters P1-P4, Shrine-Dalgarno sequence and translation initiation codon shown in FIG. 3, and the lower part of FIG. 7 shows 5'-region fragments of the cell wall protein gene inserted into the plasmid vector pHY 4833 for use in detecting promoters in relation to the said sites in the upper part. Nucleotide numbers in FIG. 7 are in accord with those in FIG. 3.

TABLE 4

| Plasmid | Extracellular amylase activity ($\times 10^3$ u/ml) Cultivation day | | |
|---|---|---|---|
| | 1 day | 2 days | 3 days |
| pHY 4833 | 0.4 | 0.4 | 0.4 |
| pTA 1 | 12.7 | 12.8 | 11.1 |
| pTA 2 | 7.8 | 7.8 | 9.8 |
| pTA 3 | 0.2 | 0.2 | 0.2 |
| pTA 4 | 5.7 | 5.1 | 6.0 |
| pTA 5 | 0.3 | 1.0 | 0.7 |
| pTA 6 | 8.0 | 8.6 | 8.0 |
| pTA 7 | 25.7 | 24.4 | 19.1 |
| pTA 8 | 1.2 | 1.5 | 1.5 |

From these results it was concluded that, in *Bacillus brevis* 47, a transcription initiation frequency occurred from the transcription initiation site P1 is very low, which site has −10 and −35 sequences similar to the consensus sequence, while, a transcription initiation frequency occurred from each of the transcription initiation sites P2, P3 and P4 is by far higher, which sites have −10 and −35 sequences dissimilar to the consensus sequence. Especially, the transcription initiation frequency from the site P3 was very high, and a transformed *Bacillus brevis* 47 carrying the plasmid pTA 7 including a fragment having P3 alone produced α-amylase in an amount 50 times as much as that produced by any of the transformed *Bacillus brevis* 47 carrying the plasmid pHY 4833 having no fragment, and the plasmid pTA 3 including P1 alone. Incidentally, the amount of intracellular amylase is less than 10% of that of extracellular amylase. The consensus sequence means the nucleotide sequence including the sequence of TTGACA in −35 region and the sequence of TATAAT in −10 region, between both sequences there being 17 base pairs.

*Bacillus brevis* 47 carrying the plasmid pTA 2 has been deposited with Fermentation Research Institute, Agency of Industrial Science and Technology as FERM P-8504 (International deposit Number FERM BP-1125)

We claim:

1. A process for expressing genes by *Bacillus brevis* which comprises transducing into a cell of *Bacillus brevis* a replicable plasmid comprising:
   (1) a nucleotide sequence (a), which is selected from the group consisting of: GCAACT, TTCACG, and TATACT;
   (2) a nucleotide sequence (b) located downstream of the nucleotide sequence (a), which is selected from the group consisting of TTTAAT, TACACT, and AAAGCG ;
   (3) a nucleotide sequence (c) located downstream of the nucleotide sequence (b) and acting as a binding site to ribosome in the cell of *Bacillus brevis*;
   (4) a nucleotide sequence (d) located downstream of the nucleotide sequence (c) and acting as a translation initiation codon in the cell of *Bacillus brevis*; and
   (5) a gene ligated in an open reading frame downstream from the nucleotide sequence (d).

2. A process for expressing genes according to claim 1, wherein the sequence (a) is GCAACT.

3. A process for expressing genes according to claim 1, wherein the sequence (a) is TTCACG.

4. A process for expressing genes according to claim 1, wherein the sequence (a) is TATACT.

5. A process for expressing genes according to claim 1, wherein the sequence (b) is TTTAAT.

6. A process for expressing genes according to claim 1, wherein the sequence (b) is TACACT.

7. A process for expressing genes according to claim 1, whereint he sequence (b) is AAAGCG.

8. A process for expressing genes according to claim 1, wherein the nucleotide sequence (c) acting as a binding site is the Shine-Dalgarno sequence.

9. A process for expressing genes according to claim 1, wherein the nucleotide sequence (d) is selected from the group consisting of ATG and TTG.

* * * * *